United States Patent [19]

Yoshimura et al.

[11] 4,283,586
[45] Aug. 11, 1981

[54] PROCESS FOR DIMERIZING OR CODIMERIZING LOWER MONOOLEFIN

[75] Inventors: Masahito Yoshimura; Satoshi Hoshiyama; Hideki Takamatsu; Hiroshi Kobayashi; Shinichiro Takigawa, all of Funabashi, Japan

[73] Assignee: Nissan Chemical Industries, Ltd., Tokyo, Japan

[21] Appl. No.: 137,260

[22] Filed: Apr. 4, 1980

[30] Foreign Application Priority Data

Apr. 11, 1979 [JP] Japan ................... 54-43759

[51] Int. Cl.$^3$ ........................... C07C 2/24; C07C 2/02
[52] U.S. Cl. ................... 585/512; 585/522; 585/523
[58] Field of Search ................. 585/512, 522

[56] References Cited

U.S. PATENT DOCUMENTS

| 3,483,268 | 12/1969 | Hambling et al. | 585/512 |
| 3,564,070 | 2/1971 | Drew et al. | 585/512 |
| 3,872,026 | 3/1975 | Dunn | 585/512 |
| 4,176,086 | 11/1979 | Carter | 585/512 |

*Primary Examiner*—Curtis R. Davis
*Attorney, Agent, or Firm*—Oblon, Fisher, Spivak, McClelland & Maier

[57] ABSTRACT

An aliphatic, cycloaliphatic or aromatic polyol is incorporated in a catalyst of an organoaluminum halide and a nickel compound. The catalyst is used for a dimerization or codimerization of a lower monoolefin to improve a reaction velocity and a stability in the reaction.

3 Claims, No Drawings

PROCESS FOR DIMERIZING OR CODIMERIZING LOWER MONOOLEFIN

BACKGROUND OF THE INVENTION

1. Field of the Invention

The present invention relates to a process for dimerizing or codimerizing a lower monoolefin in the presence of a nickel type Ziegler catalyst with a polyol.

2. Description of Prior Arts

It has been known to carry out a dimerization or codimerization of a monoolefin in the presence of a catalyst obtained from various nickel compounds and organoaluminum halides and to carry out a dimerization or codimerization of a monoolefin in the same reaction system with a small amount of water.

In these known processes, a desired result has been attained under a specific reaction condition which is precisely limited. Therefore, in an industrial continuous process for dimerizing or codimerizing a monoolefin, a satisfactory result has not been attained.

The inventors have studied processes for producing a dimer or codimer of a lower monoolefin in speedy and stable at high yield by using the catalyst obtained from various nickel compounds and organoaluminum halides.

SUMMARY OF THE INVENTION

It is an object of the present invention to provide a process for dimerizing or codimerizing a monoolefin in speedy and stable at high yield.

The foregoing and other object of the present invention have been attained by a dimerization or codimerization of a lower monoolefin in the presence of a novel catalyst comprising (1) an organoaluminum halide;
(2) at least one of nickel compounds selected from the group consisting of nickel salts of organic acid or inorganic salts, nickel complexes and nickel metal; and
(3) at least one of polyols selected from aliphatic, cycloaliphatic and aromatic polyols.

DETAILED DESCRIPTION OF THE PREFERRED EMBODIMENTS

The effect of the polyol for the mechanism of the dimerization and codimerization has not been revealed. The reason why a dimer or codimer of a monoolefin can be obtained at higher rate and higher yield by using the mixture of a nickel compound and an organoaluminum halide in the presence of a polyol than in the absence of a polyol, is considered as follows. Certain synergism of the nickel compound, the organoaluminum halide and the polyol as a novel catalyst is resulted in remarkable increase of stability of the catalyst and remarkable increase of catalytic activity.

The catalytic amount of the polyol is capable of improving the catalytic activity of the mixture of a nickel compound and an organoaluminum halide. The polyol is usually incorporated at a molar ratio of less than 2 preferably 0.01 to 1 based on the organoaluminum halide.

The conventional conditions for the reaction can be applied in the process of the present invention except incorporating the polyol. For example, the reaction is carried out with or without a conventional solvent at $-50°$ to $+100°$ C. preferably 30 to 80 under a pressure for maintaining a liquid phase such as 0.5 to 50 atm. preferably 4 to 15 atm. A ratio of the nickel compound to the organoaluminum halide can be varied and is not critical. A nickel content is preferably 0.02 to 50 especially 0.4 to 12 milli-atomic equivalent to 1 liter of the liquid phase. An atomic ratio of Al/Ni is preferably in a range of 0.02 to 500 especially 10 to 18.

In the process of the present invention, the starting material is a $C_2$–$C_8$ monoolefin such as ethylene, propylene, butene-1, butene-2 and analogous compounds having a double bond at a middle or an end, and a mixture thereof.

The catalytic component used in the process of the present invention will be illustrated.

(A) The polyols means organic compounds having two or more hydroxyl groups. The organic moiety beside hydroxyl groups can be aliphatic, cycloaliphatic or aromatic group which can be substituted by another organic group or an inorganic group.

Suitable polyols includes ethyleneglycol, 1,2-propanediol, 1,3-propanediol, 3-chloro-1,2-propanediol, 1,3-propenediol, glycerin, 1,2-butanediol, 1,3-butanediol, 1,4-butanediol, 1,4-butenediol, 1,4-butynediol, 1,5-pentanediol, 1,6-hexanediol and catechol, preferably glycols especially ethyleneglycol and butanediols.

(B) Suitable organic nickel compounds include nickel salts of carboxylic acids such as nickel formate, nickel acetate, nickel oxalate, nickel benzoate, nickel naphthenate, nickel heptanate, nickel octanate, nickel dodecanate, nickel tridecanate, nickel octadecanate.

Suitable inorganic nickel salts include nickel chloride, nickel bromide, nickel iodide, nickel fluoride, nickel nitrate and nickel sulfate.

Suitable nickel complexes include nickelocen, bisnickel acetylacetonate, nickel carbonyl, bicyclopentadienyl nickel, nickel allylchloride, bisethyl acetoacetate nickel, bisdimethylglyoxymate nickel, tetrabistriphenylphosphino nickel, tristriphenylphosphinomonocarbonyl nickel, and bistriphenylphosphinodicarbonyl nickel.

(C) The organoaluminum halides are compounds having the formula $AlR_2X$, $AlRX_2$ or $Al_2R_3X_3$ wherein R represents a $C_1$–$C_{10}$ alkyl group; and X represents a halogen atom.

Suitable organoaluminum halides include monohalodialkylaluminum, dihalomonoalkylaluminum and sesquihaloalkylaluminum such as diethylaluminum monochloride, diethylaluminum monobromide, diethylaluminum monofluoride, ethylaluminum dichloride, ethylaluminum dibromide, ethylaluminum sesquichloride, ethylaluminum sesquibromide, dipropylaluminum monochloride, dipropylaluminum monobromide, propylaluminum sesquichloride, propylaluminum dichloride and propylaluminum dibromide etc.

The reaction systems using the catalytic components (A),(B),(C) can be both a batch reaction and a continuous reaction.

The present invention will be further illustrated by certain examples and references which are provided for purposes of illustration only and are not intended to be limiting the present invention.

EXAMPLES 1 to 17

Into a 500 ml. autoclave equipped with an electromagnetic stirrer from which air and moisture were purged, 125 ml. of butane-butene fraction (butane of 20%, isobutene of 15% and n-butene of 65%) and the compounds shown in Table 1 (the amounts are also shown) were charged and each reaction was carried out under a pressure of nitrogen gas so as to maintain a liquid phase.

The reaction mixture was analyzed by a gas chromatography. Examples 2, 4, 13, 15 and 17 are out of the scope of the present invention and are shown as references. The results are also shown in Table 1.

As shown in Table 1, the yields of the dimer were lower in the cases of the catalyst system in which any polyol was not incorporated.

or nickel metal, an improvement characterized in that the catalyst further comprises at least one of aliphatic, cycloaliphatic and aromatic polyols.

2. A process according to claim 1 wherein said polyol is ethyleneglycol, 1,2-propanediol, 1,3-propanediol, 3-chloro-1,2-propanediol, 1,3-propenediol, glycerin, 1,2-butanediol, 1,3-butanediol, 1,4-butanediol, 1,4-butenediol, 1,4-butynediol, 1,5-pentanediol, 1,6-hexanediol or catechol.

3. A process according to claim 1 or 2 wherein a molar ratio of said polyol to said organoaluminum halide is less than 2 preferably in a range of 0.01 to 1.

TABLE 1

| Example | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Polyol (μl) | | | | | | | | | | | | | | | | | |
| Ethyleneglycol | 10 | — | 10 | — | 5 | 10 | 20 | — | — | — | — | — | — | 10 | — | 10 | — |
| Glycerin | — | — | — | — | — | — | — | 13 | — | — | — | — | — | — | — | — | — |
| 2,3-Butanediol | — | — | — | — | — | — | — | — | 15 | — | — | — | — | — | — | — | — |
| Catechol | — | — | — | — | — | — | — | — | — | 20 | — | — | — | — | — | — | — |
| 1,2-Cyclohexanediol | — | — | — | — | — | — | — | — | — | — | 21 | — | — | — | — | — | — |
| 1,4-Butynediol | — | — | — | — | — | — | — | — | — | — | — | 16 | — | — | — | — | — |
| Organoaluminum halide (m mol) | | | | | | | | | | | | | | | | | |
| Ethylaluminum dichloride | 1.4 | 1.4 | 1.4 | 1.4 | 1.4 | 1.4 | 1.4 | 1.4 | 1.4 | 1.4 | 1.4 | 1.4 | 1.4 | — | — | — | — |
| Diethylaluminum monochloride | — | — | — | — | — | — | — | — | — | — | — | — | — | 1.4 | 1.4 | — | — |
| Ethylaluminum sesquichloride | — | — | — | — | — | — | — | — | — | — | — | — | — | — | — | 1.4 | 1.4 |
| Nickel compound (m mol) | | | | | | | | | | | | | | | | | |
| Nickel chloride | 0.09 | 0.09 | — | — | — | — | — | — | — | — | — | — | — | — | — | — | — |
| Nickelosen | — | — | 0.91 | 0.91 | — | — | — | — | — | — | — | — | — | — | — | — | — |
| Nickel tridecanoate | — | — | — | — | 0.09 | 0.09 | 0.09 | 0.09 | 0.09 | 0.09 | 0.09 | 0.09 | 0.09 | 0.09 | 0.09 | 0.09 | 0.09 |
| Reaction temp. (°C.) | 55 | 55 | 40 | 40 | 55 | 55 | 55 | 55 | 55 | 55 | 55 | 55 | 55 | 55 | 55 | 55 | 55 |
| Dimer (g) | 34.8 | 26.5 | 23.3 | 8.7 | 35.6 | 35.0 | 38.0 | 32.9 | 31.6 | 30.0 | 32.2 | 31.0 | 25.7 | 24.8 | 3.5 | 32.2 | 11.5 |
| Reaction time (hr.) | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 |

We claim:

1. In a process for dimerizing or codimerizing a $C_2$–$C_8$ monoolefin in the presence of a catalyst comprising an organoaluminum halide and a nickel compound

* * * * *